United States Patent [19]

Schwarz et al.

[11] 4,305,799
[45] Dec. 15, 1981

[54] METHOD AND APPARATUS FOR PERFORMING UNI- AND BI-DIMENSIONAL MICRO-GEL ELECTROPHORESIS

[75] Inventors: Uli Schwarz, Tübingen; Robert Neukirchen, Biberach, both of Fed. Rep. of Germany

[73] Assignee: Max-Planck-Gesellschaft zur Förderung der Wissenschaften, e.V., Munich, Fed. Rep. of Germany

[21] Appl. No.: 167,168

[22] Filed: Jul. 9, 1980

[30] Foreign Application Priority Data

Jul. 20, 1979 [DE] Fed. Rep. of Germany ....... 2929478

[51] Int. Cl.³ ..................... G01N 27/26; G01N 27/28
[52] U.S. Cl. ............................. 204/180 G; 204/299 R
[58] Field of Search .................... 204/180 G, 299 R; 23/230 B; 424/12

[56] References Cited

U.S. PATENT DOCUMENTS

| | | |
|---|---|---|
| 3,255,100 | 6/1966 | Raymond .................... 204/180 G |
| 3,384,564 | 5/1968 | Ornstein et al. .............. 204/180 G |
| 3,445,360 | 5/1969 | Via, Jr. ....................... 204/180 G |
| 3,576,727 | 4/1971 | Evatt ........................... 204/180 G |
| 3,657,260 | 4/1972 | McLeester ................. 204/180 G X |
| 3,867,271 | 2/1975 | Hoefer ......................... 204/180 G |
| 3,901,782 | 8/1975 | Vadasz et al. ................ 204/180 G |
| 3,988,230 | 10/1976 | Krotz .......................... 204/180 G |
| 4,152,242 | 5/1979 | Makonkawkeyoon .... 204/180 G X |

*Primary Examiner*—Arthur C. Prescott
*Attorney, Agent, or Firm*—Sprung, Felfe, Horn, Lynch & Kramer

[57] ABSTRACT

The invention provides a method of performing a unidimensional and bidimensional microgel electrophoresis which method comprises first performing a unidimensional microgel electrophoresis in a capillary gel and then removing the capillary gel from its capillary tube, wherein a capillary gel rodlet obtained after said unidimensional microgel electrophoresis is disposed along one side edge of a capillary gel slab and bound to the latter and then performing the second dimension of the bidimensional microgel electrophoresis in the capillary gel slab.

17 Claims, 10 Drawing Figures

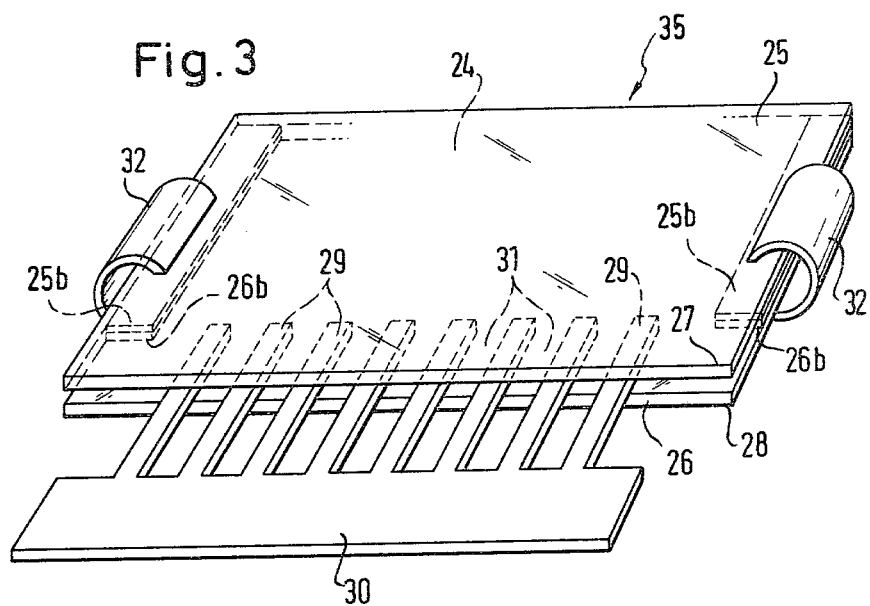
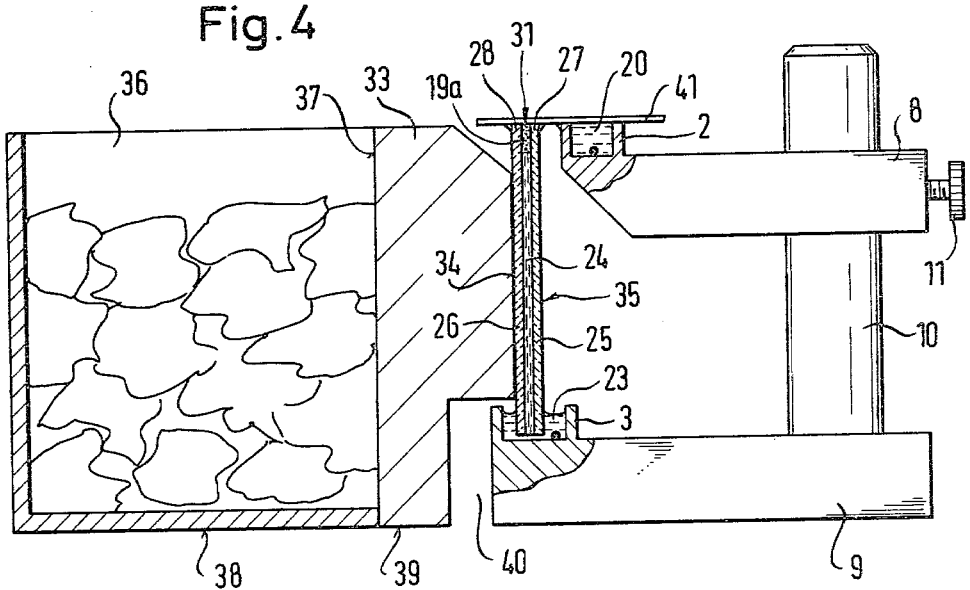

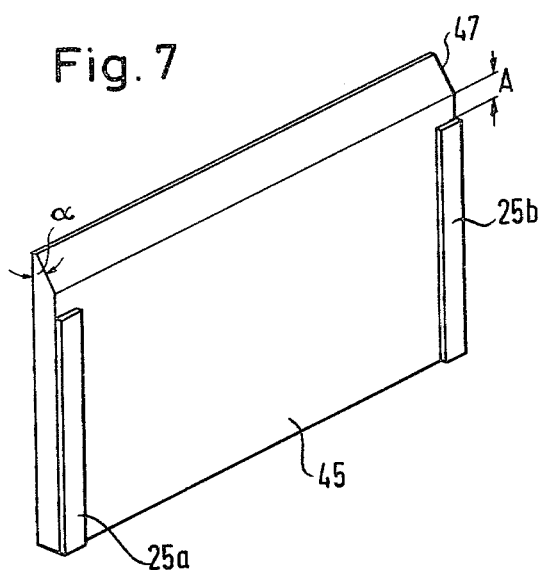
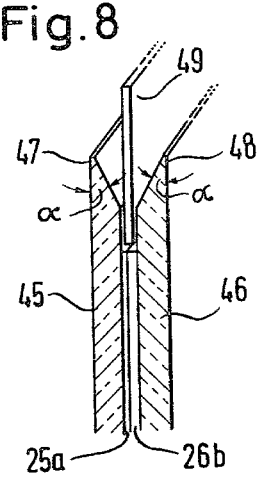
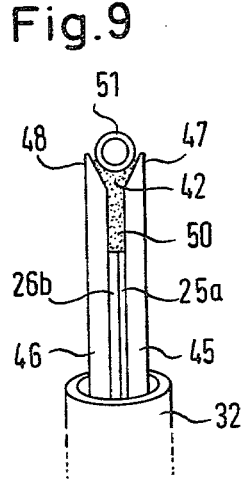
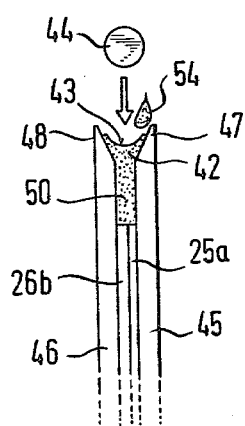

METHOD AND APPARATUS FOR PERFORMING UNI- AND BI-DIMENSIONAL MICRO-GEL ELECTROPHORESIS

The invention relates to a method of performing unidimensional and bidimensional micro-gel electrophoreses, especially of proteins and protein mixtures. More specifically, the invention provides such a method in which, first, a unidimensional micro gel electrophoresis is performed in a capillary gel, and then the capillary gel is removed from its capillary tube. In additional aspect, the invention provides an apparatus for carrying out this method.

BACKGROUND

It is known to perform gel electrophoresis for the study of proteins and protein mixtures from biological material. Proteins are separated according to their isoelectric points by isoelectric focusing, or they are separated according to molecular weight by sodium dodecyl sulfate gel electrophoresis. A combination of these two unidimensional techniques makes it possible to perform gel electrophoresis in two dimensions. This bidimensional gel electrophoresis as conventionally practiced requires a great expenditure of time, amounting to as much as two days. It also requires a high consumption of expensive reagents, such as, for example, ampholytes; furthermore, complex and expensive apparatus are required, and still furthermore a relatively large amount of sample substance is required for the performance of gel electrophoreses.

By the invention, a method and an apparatus of the kind mentioned in the beginning is to be developed, whereby the amount of time, material, apparatus and sample substance, and hence the effective cost of the performance of gel electrophoresis, will be reduced to a minimum.

THE INVENTION

In accordance with the invention, a capillary gel rodlet obtained after performance of the unidimensional micro gel electrophoresis is disposed along one lateral edge of a slab of capillary gel and joined therewith, and then the second dimension of a bidimensional micro gel electrophoresis is performed in the capillary gel slab.

An apparatus for the performance of a unidimensional and bidimensional micro gel electrophoresis in accordance with the invention is characterized by a first and second oblong fluid trough each provided in its interior with one electrode each, the troughs being disposed one above the other and parallel to one another, the lower fluid trough projecting, perpendicularly to the length of the fluid troughs, beyond the one outer long side of the upper fluid trough, so that a flat capillary body standing vertically in the lower fluid trough can extend past this one outer long side of the upper fluid trough.

In the method of the invention, and with the apparatus of the invention, in which gel slabs are used whose thickness is in the micrometer range, protein mixtures in the nanogram range can be analyzed bidimensionally in a few hours with a minimal amount of reagents and apparatus, while a considerable number of separated proteins can be obtained and hence an excellent overall analysis; furthermore, difficulties due to irregular "background" are reduced by the bidimensional separation performed on this micro scale. The method of the invention is therefore especially suitable for studies in which only a very small amount of sample substance is available. The short amount of time required permits the method to be used wherever conventional gel electrophoresis would be too time consuming, and therefore it can be used especially in series and routine testing.

The apparatus of the invention can be manufactured at relatively low cost in comparison to the expensive apparatus used for conventional gel electrophoresis, and samples as small as fractions of microliters can be tested with it.

In particular, separations and autoradiographic tests of proteins obtained in the subnanogram range from cellular material in tissue cultures by means of the micromanipulator and the microscope can be performed by the method of the invention, using the apparatus of the invention. Furthermore, it is possible to perform tests on protein samples from individual and serial sections prepared from frozen tissue specimens by means of a microtome and having a moist weight of approximately 20 micrograms and a diameter of 2 millimeters.

Presented below is a comparison of the characteristics of the gels obtained by conventional bidimensional gel electrophoresis on the one hand and by bidimensional microgel electrophoresis with capillary gel slabs on the other.

| | Comparison | | |
|---|---|---|---|
| | Conventional bidimensional gel electrophoresis | Bidimensional microgel electrophoresis with capillary gel slabs | Factor |
| Dimensions of the gel slabs (area) | 13 ×16 cm (approx. 200 sq. centimeters) | 2.4 × 3.2 cm (7.8 cm$^2$) | 25 |
| Thickness of the gels | 2 mm | 0.25 mm | 8 |
| Volume of the gels | 40 cm$^3$ | 0.2 cm$^3$ | 200 |
| Volume of solution of test substance | approx. 25 microliters | approx. 0.25 microliters | 100 |
| Run time for two dimensions | 18–24 hours | 3 hours | 6 |
| Amount of ampholytes needed | approx. 2 ml | approx. 10 microliters | 200 |
| Amount of each protein that can be detected (Coomassie blue) | approx. 1 microgram | 2–5 nanograms | 200–500 |
| Amount of stain and decolorizer solution used | approx. 500 ml | approx. 10 ml | 50 |

The invention will be further explained hereinafter with reference to FIGS. 1 to 10 of the drawing, in conjunction with a number of especially preferred embodiments.

FIG. 3 is a representation of the preparation of a capillary gel slab with pockets for the unidimensional micro gel electrophoresis;

FIG. 4 is an apparatus of the invention during a micro gel electrophoresis on a slab of capillary gel.

FIG. 7 shows a glass plate for the preparation of a capillary gel slab for the bidimensional micro gel electrophoresis;

FIGS. 8 and 9 show how a capillary gel slab is prepared for the bidimensional micro gel electrophoresis, and FIG. 10 shows how a rodlet of capillary gel with which a unidimensional micro gel electrophoresis has been performed, is placed on a capillary gel slab for the purpose of performing a bidimensional micro gel electrophoresis.

Figure 1:
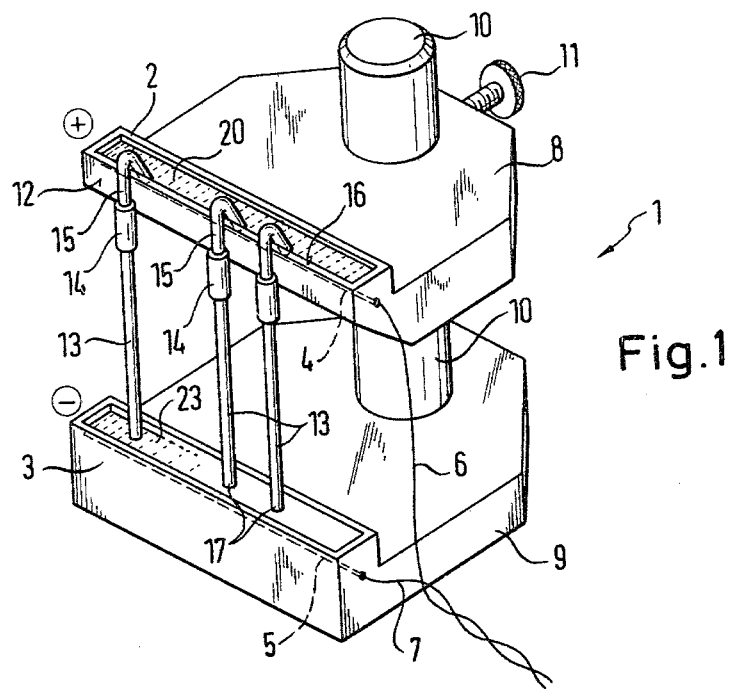
FIG. 1 is a perspective view of an apparatus of the invention in the performance of a micro gel electrophoresis using capillary gels and isoelectrical focusing.

With reference to FIG. 1, an apparatus generally identified by the numeral 1 for the performance of a unidimensional and a bidimensional micro gel electrophoresis is represented in perspective. This apparatus 1 has an upper fluid trough 2 and a lower fluid trough 3, each containing an electrode 4 or 5, preferably in the form of a rod or wire, the electrodes being connected to a power supply which is not shown in FIG. 1.

The two fluid troughs 2 and 3 serve for containing the electrode solutions, either an anode solution or a cathode solution being provided in the upper fluid trough 2, depending on the kind of micro gel electrophoresis that is to be performed. When a unidimensional micro gel electrophoresis with isoelectrical focusing is being performed, as represented in FIG. 1, the upper fluid trough 2 will contain an anode solution, whereas it will contain a cathode solution for the performance of the second step or dimension of a bidimensional micro gel electrophoresis, when this second step is to be a sodium dodecyl sulfate electrophoresis, as will be explained in greater detail further below.

The upper fluid trough 2 in the present embodiment of the apparatus 1 is integral with an upper holder 8, while the lower fluid trough 3 is integral with a lower holder 9. The two holders 8 and 9 as well as their respective integral fluid troughs 2 and 3 can be made, for example, of acrylic glass or other suitable plastic. The lower holder 9 is in the form of a stand, so that it can be set up on a work surface, such as a table top, for example.

A vertical column 10 is fastened in the lower holder 9, and the upper holder 8 is vertically displaceable thereon and can be fixed at the desired distance from the lower holder 9 by means of a locking means in the form of a setscrew, so that in this manner the distance between the two fluid troughs 2 and 3 can be adjusted as desired.

The two fluid troughs 2 and 3 have preferably a rectangular or square cross section, and their longitudinal cross section parallel to the fluid surface has preferably the shape of an elongated rectangle. The two fluid troughs 2 and 3 are disposed parallel to one another; however, the lower trough 3 is situated slightly forward of an imaginary perpendicular line descending from the outer long side 12 of the upper fluid trough 2, so that capillary tubes 13, which are coupled by a piece of flexible tubing 14 to a hook-shaped tube 15 and suspended by means of this hook-shaped tube from the upper, outer edge 16 of the upper fluid trough 2, will hang with their bottom ends 17 within the lower fluid trough 3, with the capillary tubes 13 in the vertical position.

Figure 2:
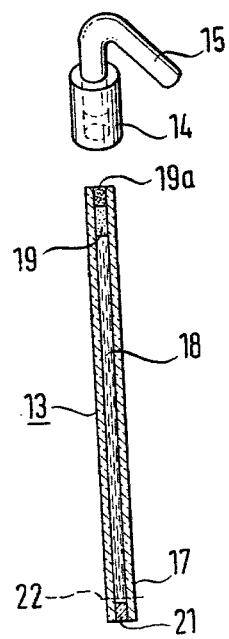
FIG. 2 is a view of a capillary tube with capillary gel and a suspension means consisting of a piece of tubing and a hook-shaped section of pipe.

The capillary tubes 13 are, as shown in FIG. 2, filled through most of their length with a capillary gel 18, which is actually the separating gel, and sample 19 for analysis is placed above the gel, and in turn is surmounted by an immersion solution whose surface reaches to the upper end of the glass capillary tube and establishes the connection with the anode solution 20 situated in the hook-shaped piece of tubing 15 and in the upper fluid trough 2.

The capillary tube 13, which is preferably of circular cross section, is represented in FIG. 2 in its state just before its preparation is completed. In this state, a plug 21 is still in the lower end of the capillary tube 13; the plug is made of a plastic composition and serves to prevent the gel solution from running out before it solidifies. Before the micro gel electrophoresis indicated in FIG. 1 is performed, the bottom end of the glass capillary tube 13, in which the plug 21 is placed, is cut off at 22, so that the capillary gel 18 at the bottom end 17 comes into direct contact with the cathode solution 23 contained in the lower fluid trough.

Another possibility for the performance of a unidimensional micro gel electrophoresis, which is especially advantageous where a large number of samples is to be analyzed, is to use, as indicated in FIGS. 3 and 4, a flat slab of capillary gel 24 sandwiched between two parallel glass plates 25 and 26 on whose confronting end margins spacer strips 25a, 25b, 26a and 26b, preferably of glass, are placed. These spacer strips terminate a few millimeters, 5 mm for example, short of the upper edges 27 and 28 of the glass plates 25 and 26, the term "upper" referring to the position in which these edges are situated during the performance of the micro gel electrophoresis, as is indicated in FIG. 4.

By the insertion of the teeth 29 of a comb-like plate 30 along the upper edges 27, 28, of the glass plates 25, 26, during the preparation of the capillary gel slab 24, pockets 31 are formed side by side in the latter and, after the comb-like plate 30 has been removed, they can be filled with a sample 19 and a covering solution 19a in much the same manner as in the case of the capillary tube 13 of FIG. 2.

The spacer strips 25a and 26a have preferably a thickness of 0.1 mm, while the spacer strips 25b and 26b have preferably a thickness of 0.15 mm, so that altogether a spacing will result between the confronting surfaces of the glass plates 25 and 26 amounting to 250 micrometers, or, in other words, a capillary gel slab 24 which is 250 micrometers thick will be formed between these glass plates.

During the preparation of the gel, the glass plates 25 and 26 are held together by laterally applied clips 32 which consist, for example, of an axially slit piece of polyethylene tubing. After gel 24 has been prepared, the clips can be removed, because then the glass plates are held together by the gel 24.

As FIG. 4 shows, the apparatus 1 also comprises a cooling block 33 of aluminum, which has a planar outer surface 34 which can be applied to the flat capillary assembly 35 that is formed by the two glass plates 25 and 26. The cooling block 33 is provided with a cooling means in the form of an ice container 36, such that the surface 37 on the side of the block opposite the planar outer surface 34 constitutes one of the inside walls of the ice container 36. The bottom surface 38 of the ice container 36 and the bottom surface 39 of the cooling block 33 are of planar configuration and lie in the same plane, so that the cooling block 33 together with the ice container 36 can, like the lower trough holder 9, be placed on a work surface, such as a table top, for example. The cooling block 33 has a rebate 40 extending over its entire length and having a height that is slightly greater than the height of the lower fluid trough 3 including its adjoining holder 9. The width of the rebate 40 is approximately equal to the width of the lower fluid trough 3.

The fluid connection between the cover solution 19a in the pockets 31 and the anode solution 20 in the upper trough 2 is established by a broad-surface capillary material 41, a sheet of filter paper, for example, which is laid on the upper edges 27, 28 of the glass plates 25, 26, on the one hand, and on the upper edges of the upper liquid trough 2 on the other hand, the latter being filled to its upper edges with the anode solution 20.

Figure 5:
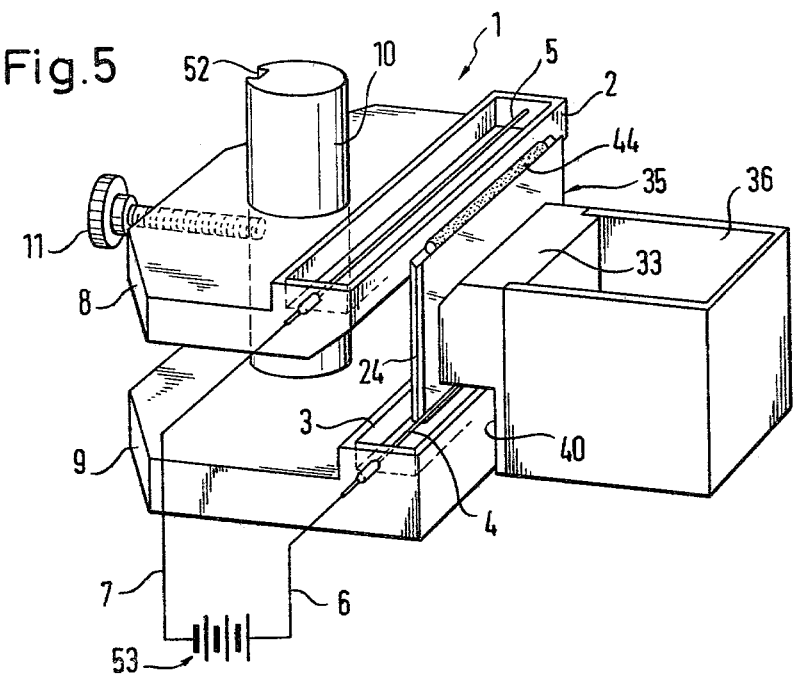
FIGS. 5 and 6 show an apparatus of the invention during the performance of a bidimensional micro gel electrophoresis, the ice tank being shown in a much smaller scale than the rest of the apparatus for the sake of clarity.
Figure 6:
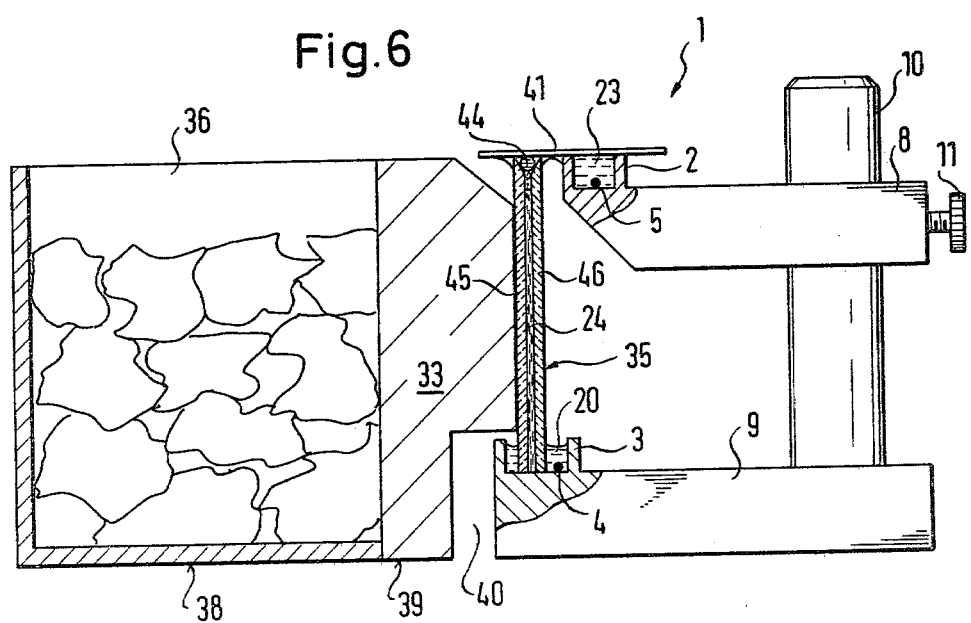

For the performance of the second step or second dimension of a bidimensional micro gel electrophoresis, which, as shown in FIGS. 5 and 6, can be performed with the same apparatus 1 as the first step or unidimensional micro gel electrophoresis, capillary gel slabs 24 in a flat capillary assembly 35 are again used, which differ from the capillary gel slabs used for the unidimensional micro gel electrophoresis of FIGS. 3 and 4 substantially in that they do not have pockets 31, but instead have a broadened upper edge 42 terminating in a concave surface 43 to accommodate a capillary gel rodlet 44. The capillary gel rodlet 44 is the product of a unidimensional micro gel electrophoresis of the kind shown in FIG. 1, although it can also be a capillary gel rodlet cut from the gel slab 24 of FIG. 3 after the performance of the unidimensional micro gel electrophoresis, in which case the surface 43 will be flattened so as to achieve a maximum surface contact with the then rectangular capillary gel rodlet and the broadened edge 42. The capillary gel rodlet 44 is placed on the broadened edge 42 with its length parallel to the length of the latter, as can best be seen in the perspective view in FIG. 5.

To form the broadened edge, glass plates 45, 46, are used, which differ from glass plates 25 and 26 substantially only in that their upper edges 47 and 48, have a bevel which encloses an angle α of 20° to 45°, preferably 30°, with the outer, planar side of each glass plate, and extend virtually over the entire thickness of glass plate 45, 46, so that the broadened upper edge 42 will have a width at its broadest point amounting to at least twice the thickness of the capillary gel slab 24. The spacer strips 25a, 25b, 26a and 26b are provided in the same manner as in FIG. 3, and their upper edges are at a distance A from the bottom end of the bevel of a few millimeters, say 2 mm, for example.

Preferably the broadened edge 42 is formed of a collector gel extending down to the level of the upper edges of the spacer strips 25a, 25b, 26a and 26b, and for this purpose, when the capillary gel slab 24 is being prepared from separating gel material, a strip 49 is inserted into this area into which the collector gel 50 will later be placed.

For the formation of a concave support surface 43, a glass capillary tube 51 is laid during the polymerization of the collector gel 50 at the place where the capillary gel rodlet 44 will later be laid. FIG. 10 shows that a good contact between the concave support surface 43 and the area of the capillary gel rodlet 44 which is laid thereon can be produced by wetting the surfaces of both with sodium dodecyl sulfate sample buffer, which can be added in very small amounts as indicated at 54 in FIG. 10.

The fluid connection between the cathode solution, which in this case is in the upper fluid trough 4, and the capillary gel rodlet 44, as required for a sodium dodecyl sulfate micro gel electrophoresis in the second dimension, is represented, in a manner similar to that illustrated in FIG. 4, by a capillary sheet material 41, which is shown only in FIG. 6, having been omitted in FIG. 5 for the purpose of clearer illustration. It is also to be noted that, in the case of the apparatus 1 in FIGS. 5 and 6, a longitudinal groove 52 is provided in the upright column 10, and is engaged by the end of the set screw of the locking means 11 that cooperates with this column, so that the two fluid troughs 2 and 3 will automatically be held always precisely parallel to one another, which is important in the case of the plate-like or sheet-like capillary gel slabs 24. Furthermore, the power source 53 is indicated in FIG. 5.

The invention will be explained in greater detail hereinbelow with the aid of several embodiments.

Examples of ampholytes for micro gel electrophoresis

Ampholytes for the isoelectrical focusing can be selected according to need, although products of a variety of manufacturers can be used with varying degrees of success. For the production of a broad pH gradient in capillary gels, a mixture of the different "Servalyts" (Serva) has proven particularly suitable:
Servalyt pH 2–4: 0.2 ml
Servalyt pH 3–5: 0.2 ml
Servalyt pH 4–6: 0.2 ml
Servalyt pH 5–7: 0.2 ml
Servalyt pH 6–8: 0.2 ml
Servalyt pH 7–9: 0.2 ml
Servalyt pH 8–10: 0.2 ml.

This mixture produces a gradient in the pH range from approximately pH 4 to pH 9 that is more uniform than when a prepared mixture is used (e.g., pH 2–11). For focusing in micro slabs, however, the broad-range ampholyte known as "Pharmalyt pH 3–10" (Pharmacia) has proven useful.

Examples of solutions for isoelectric focusing

Acrylamide stock solution
  urea: 45.0 g
  acrylamide: 5.0 g
  bis: 0.2 g
  saccharose: 12.0 g
  Triton X-100: 2.00 g
  double-distilled water to make: 100.0 ml
Anode solution
  saccharose: 6.0 g
  0.01 M phosphoric acid to make: 100.0 ml.
Cathode solution
  saccharose: 6.0 g
  0.02 M soda lye to make: 100.0 ml
Sample covering solution
  urea: 3.0 g
  ampholyte: 1.0 g
  Triton X-100: 0.2 g
  saccharose: 1.2 g
  double-distilled water to make: 10.0 ml
Sample solubilizing solution
  urea: 4.5 g ampholyte: 0.5 g
Triton X-100: 0.2 g
saccharose: 1.2 g
β-mercaptoethanol: 0.5 g
double-distilled water to make: 0.0 ml
Homogenization buffer for crude extracts of membrane
  tris 0.01 M: 0.121 g
  magnesium chloride: 0.100 g
  DNase: 0.005 g
  RNase: 0.005 g
  hydrochloric acid to pH 7.4
  double-distilled water to make: 100.0 ml.
Gel fixing solution
  methanol: 150.0 ml
  sulfosalicylic acid: 17.25 ml
  trichloroacetic acid: 57.5 g
  double-distilled water to make: 500.0 ml
Gel staining solution
  Coomassie Brillantblau R 250 (Merck): 1.0 g
  methanol: 500.0 ml
  acetic acid 96%: 100.0 ml
  double-distilled water to make: 1000.0 ml
Gel decolorizer
acetic acid 96%: 80.0 ml
ethanol 96%: 250.0 ml
double-distilled water to make: 1000.0 ml Examples of the preparation of capillary and slab gels for isoelectric focusing For capillary gels which serve as the first dimension in bedimensional electrophoresis, 25-microliter glass capillary pipettes of an inside diameter of 0.56 mm are laid for several days in laboratory cleaning agents containing alkalies and detergents. The capillaries are hot-rinsed, washed with double-distilled water and dried at 120° C. Lengths of 35 mm are then cut with a diamond glass cutter.

For the preparation of small capillary gel slabs, 1 mm thick glass plates 25 and 26 are treated with the laboratory cleaning agent and cut in half with the diamond cutter. The edges are smoothed with fine sandpaper. The 24×38 mm glass plates 25 and 26 are provided at the narrow edges with spacer strips 25a and b and 26a and b of glass 0.1 mm thick, which are cemented on. The laboratory cleaning agent improves the wettability of the glass plates and permits the gels to adhere to them. Untreated glass does not allow a uniform polymerization of the gels and therefore is unsuitable.

To prepare a capillary gel slab 24 in accordance with FIG. 3, a comb-like piece 30 having five to ten teeth 29 is inserted to a depth of about 3 mm, thus creating the pockets to contain the samples. The teeth 29 can consist of strips 1 mm wide of suitable material, so that they will not affect the polymerization of the gels, but also will not become too tightly set (damaging the gel edges).

Example of a mixture for capillary gels and gel slabs

Acrylic amide stock solution: 0.550 ml
Servalyt mixture or Pharmalyt pH 3–10: 0.025 ml
TEMED solution (10 microliters per milliliter): 0.040 ml
Ammonium peroxodisulfate solution (10 mg/ml): 0.040 ml
Effective acrylic amide content: 4.3%
Effective ampholytes: 1.6%

Example of the casting of the gels

The glass capillary sections which form the capillary molds 13 are completely filled by immersing them at an angle into the gel solution, and they are then stuck into a plasticine bed about 2 mm thick. Immediately thereafter the top 2 to 3 mm of the gel solution is removed from each tube by aspiration with a thin-drawn glass capillary to create space for the sample. The capillary gels polymerize in the upright position.

Gel slabs are cast by laying the mold flat with the comb 30 in place and using a pipette to fill completely the interstice between the glass plates 25 and 26.

All gels for the isoelectrical focusing are polymerized at room temperature and in a saturated water vapor atmosphere ("pneumatic tank"). They are ready within about two hours and are usable for as long as two days.

Example of preparation of samples for isoelectric focusing

Small tissue samples are thoroughly homogenized using homogenization buffer which stabilizes membrane components and decomposes nucleic acids. After the homogenate has been centrifuged, the membranes contained in the sediment are dissolved by homogenization in solubilizing solution. One to two microliters are sufficient for 10 micrograms of whole protein. Undissolved components are removed by centrifugation, and a small amount of saccharose, about 10%, is added to the sample, i.e., to the supernatant fluid. This increases the density and facilitates putting the samples in place (the samples will not mix together or run from their point of application). In the case of purified proteins, concentrations of from 0.1 mg/ml to 0.01 mg/ml can be used. Some proteins are detectable down to less than 5 nanograms per sample.

Example of the focusing procedure in the first dimension

The optimum electrical conditions would be a constant-power input, producing a constant heating of the gels for the duration of the run. In practice, however, a different procedure is required since apparatus for producing constant power in the microwatt and milliwatt range are virtually unavailable. Consequently a compromise is made between the thermal stress on the gels and the briefest possible run time. If a constant voltage were used, a very great heating of the gel would be produced at the beginning of the run, and the heat would diminish through the run time as the internal resistance of the gel increases. The consequence of operation at constant current would be that the thermal stress would increase constantly in the course of the focusing and excessively high voltages would occur toward the end of the run. It would, of course, be possible to keep the product "power=voltage ×current" constant by continual manual regulation, but this has proven unnecessary. The following compromise has proven acceptable for micro gel electrophoreses, and results in separations of good repeatability: In the first phase of the run, the gel is supplied with a constant current. This current is adjusted so that at the beginning there will be a resultant voltage of 30 to 40 volts. The voltage then increases over the next few minutes. As soon as 100 volts is reached, the power supply 53 is changed over to constant voltage, and a level of 100 volts is established and maintained until the end of the run. The total run time for an isoelectrical focusing amounts to about 75 minutes, of which 15 to 20 minutes represent the first (constant current) phase. If cytochrome C is used as the indicator substance, the run is considered to have ended after the cytochrome has left the bottom edge of the gel. The same applies accordingly for the focusing in capillary gel slabs.

Examples of fixing and staining

The capillary gel 18 can then be pushed slowly out of the capillary mold 13 with a steel wire using a paraffin plug as the pusher; the paraffin prevents damage to the capillary gel 18. The capillary gels are fixed in a fixing solution for 15 to 20 minutes and then washed for a few minutes in gel decolorizer until the milky gels have again become completely clear and transparent. The capillary gels are stained in stain solution diluted with decolorizer in a proportion of 1:1, and then they are decolorized. The stain solution is diluted, because otherwise the capillary gels become irreversibly distorted.

Capillary gels intended for the bidimensional electrophoresis are washed for two to three minutes in sodium dodecyl sulfate electrode buffer before the second run. Without impairing the results, the separation in the second dimension can be performed at a later period of time if the capillary gels are rapidly deep-frozen with a few drops of the SDS electrode buffer immediately after the focusing, preferably with the use of a mixture of dry ice and methanol.

Examples of solutions for a sodium dodecyl sulfate micro gel electrophoresis The sodium dodecyl sulfate micro gel electrophoresis can be performed individually (unidimensional) or bidimensionally in combination with the isoelectrical focusing. In both cases, separation is performed according to the molecular weight of the proteins in micro slabs, which are referred to as capillary gel slabs herein, and are preferably 250 micrometers thick.

acrylamide Stock Solution for Sodium Dodecyl Sulfate Gels
- acrylamide: 30.0 g
- bis: 0.8 g
- double-distilled water to make: 100.0 ml Lower Gel Buffer (Concentrate)
- sodium dodecyl sulfate: 0.2 g
- saccharose: 24.0 g
- tris: 9.1 g
- hydrochloric acid to pH 8.8
- double-distilled water to make: 100.0 ml Upper Gel Buffer (Concentrate)
- sodium dodecyl sulfate: 0.2 g
- saccharose: 24.0 g
- tris: 3.0 g
- hydrochloric acid to pH 6.8
- double-distilled water to make: 100.0 ml Sodium Dodecyl Sulfate Electrode Buffer (pH 8.3)
- tris: 0.30 g
- glycine: 1.44 g
- sodium dodecyl sulfate: 0.10 g
- saccharose: 12.0 g
- double-distilled water to make: 100.0 ml "Blue" Sample Buffer
- saccharose: 12.0 g
- glycerine: 10.0 g
- sodium dodecyl sulfate: 5.0 g
- $\beta$-mercaptoethanol: 5.0 g
- tris: 0.75 g
- hydrochloric acid to pH 6.8
- double-distilled water to make: 100.0 ml The buffer is stained with a few drops of bromophenol blue solution (2%) to make the front visible in the gel.

Mixture for 11% Separating Gels
- acrylamide stock solution: 3.65 ml
- double-distilled water: 1.35 ml
- lower gel buffer (concentrate) 5.00 ml
- Total: 10.00 ml Mixture for 4% Collecting Gels
- acrylamide stock solution: 1.30 ml
- double-distilled water: 3.70 ml
- upper gel buffer (concentrate): 5.00 ml
- Total 10.00 ml In all of the cases described, sodium dodecyl sulfate of high purity, salt-free, 99%, is used.

Example of the preparation of sodium dodecyl sulfate capillary gel slabs

The capillary gel slabs 24 for the second dimension must be prepared such that the capillary gels of the first dimension can be placed in direct contact with the collecting gel 50, which is made separately from the slab in a separate operation, without entrapping air or buffer. If the proteins should be electrophorized through a layer of buffer, the result would be a widening of the bands due to horizontal diffusion. To obtain sufficient space for the emplacement of the capillary gels, the upper edges 24 are widened, as already explained above. A size of about 15 to 50×15 to 50 mm is advantageous for the gel slab, an example being 24×36 mm.

In the case of capillary gel slabs for bidimensional separation, it is also possible to omit the collecting gel 50 entirely, that is, to cast the entire gel from a separating gel solution in a single step. In this case, the thickened edge 42 of the capillary gel slab 24 serves, together with the one drop of sodium dodecyl sulfate sample buffer 54, to replace the collecting gel 50. The saving of time and labor, however, is achieved at the cost of a certain loss of the sharpness of the protein spots. In comparison to the two-layered gels, the acrylamide content of 11% should be reduced to 9 or 10%, and the electrophoresis time must be extended by ten minutes.

To achieve a uniform polymerization, the gels are polymerized in the horizontal position. It is best to perform the polymerization in a "moist chamber" (pneumatic tank) into which an inert gas, such as nitrogen, is introduced in order to displace the atmospheric oxygen. This substantially promotes an even polymerization of the gel at the very small dimensions involved. After about 90 to 120 minutes, the polymerization has ended and the gels are ready for use.

Example of a micro gel electrophoresis in the second dimension

The capillary gel slab 24 is placed together with the glass plates 45 and 46 in the apparatus 1 (FIGS. 5 and 6), whose fluid troughs 2 and 3 are filled with sodium dodecyl sulfate electrode buffer and are placed against the icefilled cooling block 33. The capillary gel slab is to be precisely parallel to the upper liquid trough. A thin layer of buffer holds the capillary assembly 35 on the cooling block 33 and serves as a thermal conductor. The terminals of the electrodes are reversed from the polarity they had during the isoelectrical focusing.

The concave surface of the collecting gel is moistened with two drops of "blue sample buffer." The bromophenol blue makes the front visible during the electrophoresis. The high sodium dodecyl sulfate content of the sample buffer facilitates the elution of the proteins from the capillary gel rodlet 44 which contains Triton.

A freshly focused or thawed capillary gel rodlet 44, which has been washed for a few minutes in sodium dodecyl sulfate electrode buffer, is placed on the collecting gel 50.

Samples for the bidimensional sodium dodecyl sulfate gel electrophoresis are prepared by boiling in sample buffer in a conventional manner. The addition of saccharose increases the density of the sample. The placement of the sample in the capillary assembly is performed in a manner similar to the focusing operation, as explained in connection with FIGS. 1 to 4, and the space remaining above the sample is filled with electrode buffer.

The sodium dodecyl sulfate gel electrophoresis is performed under electrical conditions similar to those of the focusing. Beginning with constant current and a resultant effective voltage of 40 volts, the voltage increases in the course of about 15 minutes to 100 volts. The power supply is changed over to constant voltage at 100 volts, and the electrophoresis is continued with diminishing current.

Example of Fixation and Staining

After the micro gel electrophoresis, the two glass plates 45 and 46 are separated and the capillary gel slab together with the adhering glass plate is fixed for 15 to 20 minutes in fixer, floated off from the glass and washed clear with decolorizer. Then it is stained in the dye solution for 20 to 30 minutes, and then decolorized. Unidimensional sodium dodecyl sulfate capillary gels and gel slabs can be stained immediately without fixing.

It will be understood that the specification and examples are illustrative but not limitative of the present invention and that other embodiment within the spirit and scope of the invention will suggest themselves to those skilled in the art.

What is claimed is:

1. Method of performing a unidimensional and bidimensional microgel electrophoresis which method comprises first performing a unidimensional microgel electrophoresis in a capillary gel and then removing the capillary gel from its capillary tube, wherein a capillary gel rodlet obtained after said unidimensional microgel electrophoresis is disposed along one side edge of a capillary gel slab and bound to the latter and then performing the second dimension of the bidimensional microgel electrophoresis in the capillary gel slab.

2. Method as claimed in claim 1 wherein the capillary gel rodlet is bound to the capillary gel slab by being laid directly into the collector gel.

3. Method as claimed in claim 1 wherein the capillary gel rodlet is laid upon a side edge of the capillary gel slab, which side edge is formed from separating gel and is thickened.

4. Method as claimed in claim 2 wherein the capillary gel rodlet is bound by means of a buffer solution as a wetting bond to the collector gel.

5. Method as claimed in claim 2 wherein a capillary gel rodlet of rounded cross section is used and the supporting surface of the collector gel or of the thickened side edge formed of separating gel of the capillary gel slab, on which the capillary gel rodlet is laid, is of concave shape.

6. Method as claimed in claim 1 wherein the unidimensional microgel electrophoresis is performed in a capillary gel slab on whose one side edge a plurality of samples are applied at intervals extending lengthwise of the side edge.

7. Method as claimed in claim 6 wherein pockets extending transversely of and preferably perpendicular to the side edge of the capillary gel slab are provided in the capillary gel slab and the individual samples are placed in these individual pockets.

8. Method as claimed in claim 1 wherein the unidimensional microgel electrophoresis is performed in a rod shaped capillary gel of rounded cross section.

9. Method as claimed in claim 1 wherein capillary gel slabs of a thickness of less than 500 micrometers are used.

10. Method as claimed in claim 9 wherein capillary gel slabs of a thickness of 200 to 300 micrometers are used.

11. Method as claimed in claim 1 wherein the unidimensional microgel electrophoresis is performed with iso-electrical focusing.

12. Method as claimed in claim 1 wherein the second dimension or bi-dimensional microgel electrophoresis is performed as a sodium dodecyl sulfate electrophoresis.

13. Method as claimed in claim 1 wherein the first unidimensional microgel electrophoresis is performed first for a predetermined length of time with constant current and then it is performed at constant voltage for the rest of the time.

14. Method as claimed in claim 13 wherein the second dimension of the bidimensional microgel electrophoresis is performed first for a predetermined length of time with constant current and then it is performed at constant voltage for the rest of the time.

15. Method as claimed in claim 13 wherein the predetermined length of time amounts to approximately 20 to 30% of the total duration of the microgel electrophoresis.

16. Method as claimed in claim 13 wherein the microgel electrophoresis is begun at a voltage of 30 to 40 volts and is performed at constant current until the voltage has rises to 90 to 100 volts, and thereafter it is continued at constant voltage.

17. Method as claimed in claim 1 wherein capillary gel slabs polymerized in the horizontal position are used.

* * * * *